United States Patent [19]

Gramlich et al.

[11] 4,347,388
[45] Aug. 31, 1982

[54] 3,6-DIMETHYL-3-HYDROXY-OCT-1-YNES AND -OCT-1-ENES, DERIVATIVES OF THESE, AND THEIR USE AS SCENTS, AND IN THE PREPARATION OF 3,6-DIMETHYL-3-HYDROXY-OCTANE

[75] Inventors: Walter Gramlich, Edingen; Werner Hoffmann, Neuhofen; Leopold Hupfer, Friedelsheim; Bernd Meissner, Heidelberg; Juergen Paetsch, Wachenheim, all of Fed. Rep. of Germany

[73] Assignee: BASF Aktiengesellschaft, Ludwigshafen, Fed. Rep. of Germany

[21] Appl. No.: 279,801

[22] Filed: Jul. 2, 1981

[30] Foreign Application Priority Data

Jul. 18, 1980 [DE] Fed. Rep. of Germany ....... 3027269

[51] Int. Cl.$^3$ ................ C07C 33/02; C07C 33/03; C07C 69/145; C07C 69/24
[52] U.S. Cl. ................ 568/840; 252/522 R; 560/261; 568/878; 568/903
[58] Field of Search ............ 568/873, 875, 840; 560/249, 261

[56] References Cited

U.S. PATENT DOCUMENTS 2,815,379  12/1957  Surmatis ............... 568/873
2,918,412  12/1959  Wood ................... 568/873
3,082,216  3/1963   Dimroth et al. ......... 568/873
3,634,054  1/1972   Stalego ................ 568/873
3,700,740  10/1972  Mourier ................ 568/875

FOREIGN PATENT DOCUMENTS 1031075  5/1966  United Kingdom ............... 568/873

Primary Examiner—Joseph E. Evans
Attorney, Agent, or Firm—Oblon, Fisher, Spivak, McClelland & Maier

[57] ABSTRACT

3,6-Dimethyl-3-hydroxy-oct-1-ynes and -oct-1-enes and their esters with lower alkanoic acids, of the general formula I

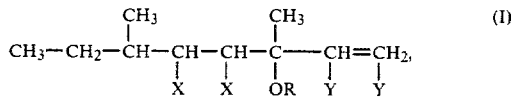

where X and Y are H or the two X's and/or the two Y's together are a further bond between the carbon atoms on which they are present, and R is H, —CO—CH$_3$, —CO—C$_2$H$_5$ or —CO—C$_3$H$_7$, their use as scents, and a process for the preparation of 3,6-dimethyl-3-hydroxy-octane. The novel compounds exhibit interesting, predominantly floral, woody, herbal and fruity notes. The alcohols of the formula I are of particular importance because they serve as intermediates for a novel and particularly advantageous method of obtaining 3,6-dimethyl-3-hydroxy-octane, a compound required in large amounts as a fragrance for soaps and detergents.

3 Claims, No Drawings

3,6-DIMETHYL-3-HYDROXY-OCT-1-YNES AND -OCT-1-ENES, DERIVATIVES OF THESE, AND THEIR USE AS SCENTS, AND IN THE PREPARATION OF 3,6-DIMETHYL-3-HYDROXY-OCTANE

The present invention relates to 3,6-dimethyl-3-hydroxy-oct-1-ynes and -oct-1-enes, which may or may not be olefinically unsaturated in the 4,5-position, to their esters with lower alkanoic acids, to their use as scents, and to a process for the preparation of 3,6-dimethyl-3-hydroxy-octane from the novel alcohols. The novel compounds have the general formula I

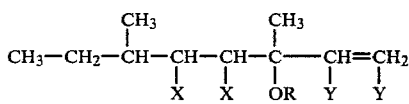

where X and Y are H or the two X's and/or the two Y's together are a further bond between the carbon atoms on which they are present, and R is H, —CO—CH₃, —CO—C₂H₅ or —CO—C₃H₇.

The novel compounds have interesting, predominantly floral, woody, herbal and fruity notes and accordingly enrich the range of available valuable fully synthetic fragrances.

The novel compounds are of particular importance because they serve as intermediates for a novel and particularly advantageous method of obtaining 3,6-dimethyl-3-hydroxy-octane, a compound required in large amounts as a fragrance for soaps and detergents. This method of synthesis is possible because on the one hand the novel compounds can be prepared relatively simply from readily accessible starting compounds, whilst on the other hand they are simple to convert to the desired 3,6-dimethyl-3-hydroxy-octane.

The starting materials for the preparation of the novel compounds are 5-methyl-hept-3-en-2-one and 5-methyl-heptan-2-one, which are simple to prepare by condensing 2-methyl-butanol and acetone, with or without simultaneous or subsequent hydrogenation of the olefinic double bond. 2-Methyl-butanol for its part, is obtainable by hydroformylating but-1-ene or but-2-ene.

The compounds of the formula I, where R is H and the Y's are an additional bond are obtained, for example, by reacting 5-methyl-hept-3-en-2-one or 5-methyl-heptan-2-one, ie. a ketone of the general formula II

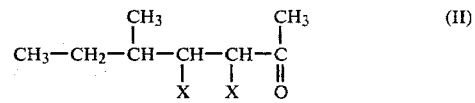

where the X's have the above meanings, with a solution of an ethynyl-magnesium halide in tetrahydrofuran or dimethyl ether, or with acetylene in the presence of a catalyst.

The compounds of the formula I, where R is H and the Y's are H are obtained, for example, by reacting a ketone of the formula II with a solution of a vinyl-magnesium halide or by partially hydrogenating the triple bond of an alkynol obtained on ethynylating a ketone of the formula II. These reactions are shown in the following equations:

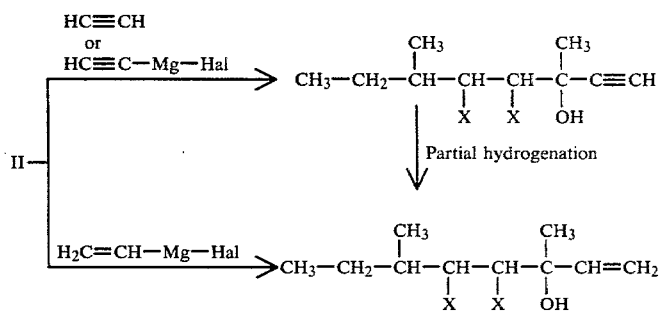

The esterification of the hydroxyl group can be carried out either as a final reaction or prior to any partial hydrogenation.

3,6-Dimethyl-3-hydroxy-octane, a greatly sought-after scent, can be prepared in a simple manner from the alcohols of the general formula I by catalytic hydrogenation. Accordingly, the invention also relates to a process for the preparation of 3,6-dimethyl-3-hydroxyoctane, wherein a ketone of the general formula II

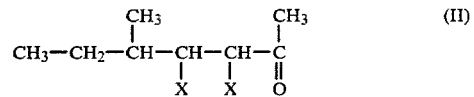

where the X's are H or the two X's together are a further bond between the carbon atoms on which they are present, is reacted with a solution of an ethynyl-magnesium halide or vinyl-magnesium halide in an ether solvent, or is reacted with acetylene in the presence of a catalyst, and the resulting novel compound of the general formula Ia

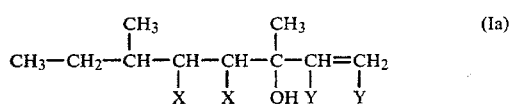

where the X's and the Y's have the above meanings, is catalytically hydrogenated in a conventional manner.

The reactions are all carried out in a conventional manner, so that no detailed information concerning the reaction conditions need be given.

The ethynylation is carried out either by reacting a ketone of the formula II with a solution of an ethynyl-magnesium halide in tetrahydrofuran or diethyl ether, or by reacting a ketone II with acetylene in an inert organic solvent in the presence of a heavy metal acetylide, eg. copper acetylide or silver acetylide, or in the presence of a basic catalyst, such as sodium acetylide, potassium acetylide or an alkali metal or alkaline earth metal oxide, hydroxide, alcoholate, hydride or amide, or in the presence of an anion exchanger containing quaternary ammonium groups (cf., for example, Belgian Pat. No. 725,275).

The ethynylation is carried out at from −20° to +70° C., preferably from 10° to +50° C., under pressures ranging from atmospheric pressure to about 30 atmospheres. The mixture is worked up, and the reaction product isolated, by hydrolysis followed by fractional distillation of the organic phase.

The partial hydrogenation of the alkynol obtained can be carried out in the presence or absence of a solvent.

Particularly suitable catalysts are supported palladium catalysts which contain from 0.01 to 5 percent by weight of palladium.

Specific examples of the catalyst carriers are calcium carbonate, barium hydroxide, aluminum oxide and silicon dioxide. To increase the selectivity, it is advisable to deactivate the said catalysts, for example by treatment with zinc ions or lead ions as described in German Pat. No. 1,115,238.

The hydrogenation is in general carried out under atmospheric pressure, or under an excess pressure of hydrogen of from 0.1 to 1 atmosphere, and at from about 0° to 80° C., preferably from 15° to 35° C. The reaction products are isolated by filtration and distillation.

The reaction of a ketone of the formula II with a solution of a vinyl-magnesium halide is carried out in the conventional manner of carrying out Grignard reactions, advantageously using an about 1-2 molar solution of vinyl-magnesium chloride in an ether solvent, such as diethyl ether, tetrahydrofuran or diethylene glycol dimethyl ether, at from −20° to +50° C.

The ester group can also be introduced by various conventional methods.

For example, the alkynol obtained by ethynylation can be esterified with a carboxylic acid anhydride in the presence of a catalytic amount of a mineral acid, such as sulfuric acid or phosphoric acid, with or without subsequent partial hydrogenation of the ester obtained.

The alkenols obtained by vinylation can advantageously be reacted with an acyl halide of the formula R-halogen in the presence of an acid acceptor, such as trimethylamine or dimethylaniline, or be trans-esterified with tert.-butyl acetate, propionate or butyrate in the presence of sodium methylate or potassium tert.-butylate.

The catalytic hydrogenation of an alcohol of the formula Ia to give 3,6-dimethyl-octan-3-ol is carried out in a conventional manner, and using a conventional hydrogenating catalyst, for example a palladium or platinum catalyst.

Supported palladium catalysts, such as $Pd/SiO_2$, $Pd/Al_2O_3$, Pd/charcoal and the like, are particularly suitable. Advantageously, the hydrogenation is carried out in a solvent which is inert under the reaction conditions, such as methanol, ethyl acetate or tetrahydrofuran, at from 20° to 120° C. and under an absolute hydrogen pressure of from 0 to 50 atmospheres.

The products can all be isolated in a pure form by distillation.

The 3,6-dimethyl-3-hydroxy(acyloxy)-oct-1-ynes and -oct-1-enes according to the invention are valuable scents, which are predominantly suitable for the preparation of floral, herbal and fruity compositions. In addition, they offer a novel and particularly advantageous method for the synthesis of 3,6-dimethyl-3-hydroxyoctane, a highly sought-after fragrance for soaps and detergents.

EXAMPLE 1

3,6-Dimethyl-oct-1-yn-3ol (1 c)

128 g (1 mole) of 5-methyl-heptan-2-one are added in the course of 1 hour, with stirring, to 1 liter of a 1.1 molar solution of ethynyl-magnesium chloride in tetrahydrofuran at 10° C. After allowing about a further hour's reaction, the mixture is worked up. To do so, 2 N sulfuric acid is added, whilst cooling with ice, until two clear phases are present. The organic phase is then separated off and washed neutral with water, if necessary, and the tetrahydrofuran is distilled off at 50° C./67 mbar. The residue is subjected to fractional distillation. 143 g of main fraction, boiling at 50°–52° C./0.01 mbar, are obtained; $n_D^{25} = 1.4411$. This corresponds to a yield of 93%. Scent: predominantly floral, woody, herbal, minty with a spicy, slightly animal after-scent.

EXAMPLE 2

3,6-Dimethyl-oct-1-en-3-ol (1 d)

154 g (1 mole) of 3,6-dimethyl-oct-1-yn-3ol are dissolved in 100 ml of methanol, 1 g of an 0.1% strength palladium/calcium carbonate catalyst, which has been poisoned with zinc ions, is added, and hydrogen is passed in at 20° C. under atmospheric pressure. The hydrogenation is complete in 6 hours, when about 24 liters of hydrogen have been absorbed.

The catalyst is filtered off, the methanol is distilled off at 50° C./67 mbar, and the product is fractionated. 146 g of main fraction, boiling at 46°–48° C./0.1 mbar, are obtained; $n_D^{25} = 1.4407$. This corresponds to a yield of 94%. Scent: predominantly floral, woody, herbal, with a minty, sweet after-scent.

EXAMPLE 3

3,6-Dimethyl-octan-3-ol 0.5 g of an 0.5% strength palladium/aluminum oxide catalyst is added to 154 g (1 mole) of 3,6-dimethyl-oct-1-yn-3-ol and hydrogenation is carried out at 20°–50° C. and 0.5 bar hydrogen pressure. When hydrogen absorption has ceased (after 6–8 hours), the catalyst is filtered off and the filtrate is fractionated. 145 g of main fraction, boiling at 42°–43° C./0.01 mbar, are obtained; $n_D^{25} = 1.4345$. This corresponds to a yield of 91%. Scent: fresh, floral, lavender-like.

EXAMPLE 4

3,6-Dimethyl-oct-4-en-1-yn-3-ol 126 g (1 mole) of 5-methyl-hept-3-en-2-one are added in the course of 1 hour, with stirring, to 1 liter of a 1.1 molar solution of ethynyl-magnesium chloride in tetrahydrofuran, at 10° C. After allowing about a further hour for reaction, the mixture is worked up similarly to Example 1. 126 g of 3,6-dimethyl-oct-4-en-1-yn-3-ol, of boiling point 41° C./0.05 mbar and $n_D^{25} = 1.4514$, are obtained. This corresponds to a yield of 83% of theory. Scent: woody, herbal, fatty.

EXAMPLE 5

3,6-Dimethyl-octa-1,4-dien-3-ol 154 g (1 mole) of 3,6-dimethyl-oct-1-yn-4-en-3-ol are dissolved in 100 ml of methanol, 1 g of an 0.1% strength palladium/calcium carbonate catalyst, which has been poisoned with zinc ions, is added, and hydrogen is passed in at 15°–20° C. under atmospheric pressure. After 6 hours, the mixture is worked up similarly to Example 2. 145 g of 3,6-dimethyl-octa-1,4-dien-3-ol, of boiling point 38°–39° C./0.01 mbar and $n_D^{25}=1.4502$, are obtained. This corresponds to a yield of 93% of theory.

Scent: woody, fatty, minty, slightly animal.

EXAMPLE 6

3,6-Dimethyl-3-acetoxy-oct-4-en-1-yne 153 g of acetic anhydride, in which 0.5 g of 85% strength phosphoric acid has been dissolved, are added to 172 g (1.13 moles) of 3,6-dimethyl-oct-4-en-1-yn-3-ol, and the reaction mixture is stirred for about 16 hours at 20°–25° C. It is then taken up in about 500 ml of ether, this solution is washed neutral with water and sodium carbonate solution, and the solvent is distilled off at 30° C./20 mm Hg. The reaction product which remains is fractionated, giving 169 g of the acetate, corresponding to a yield of 77% of theory. Boiling point 51°–52° C./0.01 mbar; $n_D^{25}=1.4606$.

Scent: sweetish, resembling cinnamyl alcohol.

EXAMPLE 7

3,6-Dimethyl-3-acetoxy-octa-1,4-diene 87 g (0.5 mole) of 3,6-dimethyl-3-acetoxy-oct-4-ene-1-yne are hydrogenated, similarly to Example 2, at 15°–20° C. After working up, and distillation, 76 g of 3,6-dimethyl-3-acetoxy-octa-1,4-diene, of boiling point 105°–106° C./15 mbar and $n_D^{25}=1.4550$, are obtained. This corresponds to a yield of 87% of theory.

Scent: woody, resembling cinnamyl alcohol.

EXAMPLE 8

3,6-Dimethyl-3-acetoxy-oct-1-yne 154 g (1 mole) of 3,6-dimethyl-oct-1-yn-3-ol are esterified with acetic anhydride, similarly to Example 6. After working up and distillation, 178 g of the acetate are obtained, corresponding to a yield of 91%. Boiling point 44°–45° C./0.01 mbar; $n_D^{25}=1.4352$.

Scent: floral, woody, resembling cedarwood, slightly herbal.

We claim:

1. 3,6-Dimethyl-3-hydroxy-oct-1-ene and its derivatives, of the general formula I

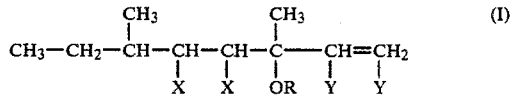

where X and Y are H or the two X's and/or the two Y's together are a further bond between the carbon atoms on which they are present, and R is H, —CO—CH$_3$, —CO—C$_2$H$_5$ or —CO—C$_3$H$_7$.

2. 3,6-Dimethyl-3-hydroxy-oct-1-yne.
3. 3,6-Dimethyl-3-hydroxy-oct-1-ene.

* * * * *